United States Patent [19]

Blank et al.

[11] Patent Number: 4,760,093

[45] Date of Patent: Jul. 26, 1988

[54] SPRAY DRIED ACETAMINOPHEN

[75] Inventors: Robert G. Blank, Vineland; Dhiraj S. Mody, Hammonton; Gary R. Agism, Cherry Hill; Richard J. Kenny, Sommerset, all of N.J.

[73] Assignee: American Home Products Corporation (Del.), New York, N.Y.

[21] Appl. No.: 921,557

[22] Filed: Oct. 21, 1986

[51] Int. Cl.$^4$ .................... A61K 31/74; A61K 31/78
[52] U.S. Cl. .................................. 514/629; 424/81; 424/497
[58] Field of Search ................... 424/81, 497; 514/629

[56] References Cited

U.S. PATENT DOCUMENTS 4,562,024 12/1985 Rogerson ............................ 514/629
4,631,284 12/1986 Salpekar et al. .................... 514/629

OTHER PUBLICATIONS

Eudragit TM E, Application in the Production of Pharmaceutical Preparations a publication of Rohm Pharma GMBH, printed 2/84.

Eudragit TM E 100, Data Sheet, a publication of Rohm Pharma GMBH, printed 2/84.

Eudragit TM E, Technical Application Pamphlet, Production of Taste-proof, Coloured Film-coated Tablets in Coating Pans, Rohm Pharma GMBH, printed 9/84.

Eudragit TM E, Technical Application Pamphlet, Coating of Small Particles in the Fluidized Bed Process, Rohm Pharma GMBH, printed 3/83.

Primary Examiner—Joseph L. Schofer
Assistant Examiner—Peter F. Kulkosky
Attorney, Agent, or Firm—John W. Routh

[57] ABSTRACT

A therapeutic taste-neutral powder form of acetaminophen obtained by spray-drying a suspension of acetaminophen in a solution of a particular copolymer, cationic in character, based on dimethylaminoethyl methacrylate and neutral methacrylic acid esters.

6 Claims, No Drawings

SPRAY DRIED ACETAMINOPHEN

BACKGROUND OF THE INVENTION (a) Field of the Invention

This invention relates to a novel therapeutic form of spray dried acetaminophen having a neutral taste which can be formulated into for example, fast dissolving dosage forms as described in U.S. Pat. Nos. 4,305,502 and 4,371,516. More specifically this invention relates to a taste neutral spray dried powder formed by spray drying a suspension of acetaminophen in a solution of a copolymer, cationic in character, based on dimethylaminoethyl methacrylate and neutral methacrylic acid esters having a mean molecular weight of 150,000. By taste-neutral it is meant that the powder has essentially no taste and is not sweet nor bitter.

(b) Prior Art

One of the copolymers useful in this invention is commercially available as Eudragit E 100 from Rohm Tech, Inc., 195 Canal Street, Malden MA 02148, United States representative of Rohm Pharma GmbH, Weiterstadt West Germany.

The fast dissolving dosage forms described in U.S. Pat. Nos. 4,305,502 and 4,371,516 are manufactured to disintegrate in water within five seconds or less and hence dissolve rapidly in the saliva of the mouth. Heretofore the use of such dosage forms was restricted to pharmaceuticals which had a neutral taste or a slightly disagreeable taste which could be masked by a flavoring agent. Pharmaceuticals with a bitter taste such as acetaminophen and ibuprofen, however, could not heretofore be used in such dosage forms.

SUMMARY OF THE INVENTION

According to this invention, a novel therapeutic taste-neutral powder form of spray-dried acetaminophen is provided which can be formulated into fast dissolving dosage forms, chewable tablets and the like. The powder is formed by spray drying a solution having dissolved therein a copolymer, cationic in character, having a mean molecular weight of 150,000, based on dimethylaminoethyl methacrylate and neutral methacrylic acid esters, the solution having finely divided acetaminophen suspended therein.

According to another aspect of this invention, a pharmaceutical dosage form for oral administration as a solid is provided, which dosage form can be disintegrated by water at 37° C. within ten seconds, and comprises as the pharmaceutical agent incorporated therein the taste neutral powder form of spray dried acetaminophen of this invention.

Details of the Invention

The acetaminophen useful in this invention is the pharmaceutical grade. The copolymer is available as Eudragit E 100 from Rohm Pharma GmbH, Darmstadt, West Germany as light yellow granules containing at least 98% of dry lacquer substance having an acid value of 180 mg KOH/g. The structural formula is:

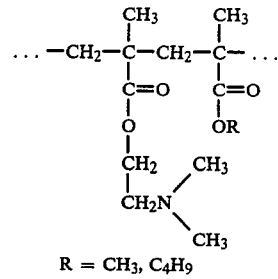

$R = CH_3, C_4H_9$

The weight percent of acetaminophen in the taste neutral powder can be from about 60 to 74% by weight and the weight percent of the copolymer can range from 26% to 40% by weight. At 26% by weight of copolymer, there is a slightly bitter taste but at 30% and above the powder is taste neutral.

The solvent for the copolymer can be, for example, methylene chloride, acetone, or an alkanol but must be an organic solvent selective for the copolymer and in which the acetaminophen is not soluble to any great extent.

Spray dryers can be of the usual laboratory or commercial type. Suitable spray dryers are manufactured by Buchi Laboratoriums-Technik AG, by the Anhydro Company of Attleboro, Mass. and by Niro Atomizer Inc., of Columbia, Md.

The spray dryer employed in the following examples was a Niro Portable Spray Dryer, Model No. 21231-0001. The operating conditions include a variable air inlet temperature, a variable outlet temperature, a variable air pressure of compressed air driving the atomizer wheel, and a variable feed rate.

The following examples illustrate the formation of the taste-neutral spray dried acetaminophen powder of the invention.

EXAMPLE I

In this example, the feed mixture to the spray dryer was composed of the following materials.

| Ingredient | Weight % Ingredient in Suspension | Weight % Solids in Suspension | Weight % Solids in powder | Grams Ingredient in suspension |
|---|---|---|---|---|
| Acetaminophen | 4.50 | 4.50 | 70.09 | 270 |
| Methylene chloride | 73.58 | — | — | 4414.8 |
| Eudragit E-100 | 1.92 | 1.92 | 29.91 | 115.2 |
| Methylene Chloride | 20.00 | — | — | 1200 |
| Total: | 100.00 | 6.42 | 100 | 6000 g. |

The acetaminophen was suspended in the 4414.8 grams of methylene chloride contained in a stainless steel mixing vessel with the aid of a Lightnin mixer. The Eudragit E-100 was dissolved in the remaining methylene chloride in a separate stainless steel mixing vessel and the contents of the two mixing vessels were then admixed and transferred to the feed hopper of the Niro Portable Spray Dryer.

The spray drier was operated with a feed rate of 60 grams per minute and initially at ambient inlet air temperatures. The air presssure was 4.8 bar. After a first chamber sweep, the chamber powder was observed to be slowly adhering to the walls and had a definite solvent odor. The air inlet heater was turned on so as to produce an outlet temperature of 25°–30° C. The powder from a second chamber sweep had less solvent odor and no powder adherence was noted.

The yield of spray dried powder was 91.12%, 140 grams from the cyclone and 211 grams from the chamber. The product from the cyclone was a white, fine powder and the product from the chamber was a fine white powder but not free-flowing.

The product from the cyclone, when tasted, produced no bitterness characteristic of acetaminophen but a slight solvent odor and taste. The product from the chamber produced a very slight bitterness with only a slight solvent odor and taste.

EXAMPLE 2

In this example, the solids content of the suspension was increased as follows:

| Ingredient | Weight % Ingredient in Suspension | Weight % Solids in Suspension | Weight % solids in powder | Grams Ingredient in suspension |
|---|---|---|---|---|
| Acetaminophen | 13.50 | 13.50 | 70.09 | 270.0 |
| Methylene chloride | 30.74 | — | — | 614.8 |
| Eudragit E-100 | 5.76 | 5.76 | 29.91 | 115.2 |
| Methylene Chloride | 50.00 | — | — | 1000.0 |
| Total: | 100.00 | 19.26 | 100.00 | 2000.0 g |

The spray dryer was operated with a feed rate of 80 grams per minute with an air pressure of 4.6 bar declining to 3.8 bar. The air inlet heater was turned on so as to produce an outlet temperature of 25° to 30° C. with an air pressure of 4.6 bar declining to 3.8 bar.

The yield of spray dried product was 304.1 grams, 158.6 grams from the cyclone and 145.5 grams from the chamber, which is 78.95% of the theoretical yield.

The product from each of the cyclone and the chamber, when tasted produced no bitterness in the mouth. There was a very slight taste and odor of solvent.

Dissolution data were obtained on capsules containing the spray dried product of this example using the USP procedure and using gastric juice. The spray dried product in the amount of 114.5 milligrams containing 80 milligrams of acetaminophen was placed in each capsule and six capsules were used in each test. In the USP procedure at a pH of 5 to 7, the data show that at least 94% of the control dissolved in 10 minutes while no more than 10% of the spray dried product dissolved in 10 minutes. In the procedure using gastric juice instead of water, 80% of the spray dried product dissolved in less than 10 minutes.

EXAMPLE 3

In this example, the feed mixture to the spray dryer was composed of the following materials.

| Ingredient | Weight % Ingredient in Suspension | Weight % Solids in Suspension | Weight % Solids in powder | Grams Ingredient in 500 grams suspension |
|---|---|---|---|---|
| Acetaminophen | 4.50 | 4.50 | 73.77 | 22.50 |
| Methylene chloride | 77.90 | — | — | 389.50 |
| Eudragit E-100 | 1.60 | 1.60 | 26.23 | 8.00 |
| Methylene Chloride | 16.00 | — | — | 80.00 |
| Total: | 100.00 | 6.10 | 100 | 500.00 grams |

The acetaminophen was suspended in the first portion of methylene chloride contained in a stainless steel mixing vessel with the aid of a Lightnin mixer. The Eudragit E-100 was dissolved in the remaining methylene chloride in a separate stainless steel mixing vessel and the contents of the two mixing vessels were then admixed and transferred to the feed hopper of the Niro Portable Spray Dryer.

The spray drier was operated with a feed rate of 65 grams per minute and initially at ambient inlet air temperatures. The air pressure was 4.6 bar.

The yield of spray dried powder was 78.13%, 6.16 grams from the cyclone and 17.67 grams from the chamber. The product was a fine white, free-flowing powder.

The product, when tasted, produced a very slightly bitter taste characteristic of acetaminophen and a slight odor and taste.

EXAMPLE 4

This example describes the preparation of fast dissolving dosage forms using the spray dried taste-neutral acetaminophen of Example 1 and other ingredients as follows:

| Ingredients | Weight % suspension | Grams in suspension |
|---|---|---|
| Gelatin, BY 19/50 | 4.0 | 10.00 |
| Mannitol, granular | 3.0 | 7.50 |
| Deionized water | 67.10 | 167.75 |
| NUTRASWEET, NF | 1.20 | 3.00 |
| Cherry #271 | 0.40 | 1.00 |
| Cream Flavor #59.200/A | 0.20 | 0.50 |
| Sodium laurylsulfate | 0.10 | 0.25 |
| Croscarmellose sodium, Type A | 1.00 | 2.50 |
| Powder, Example 1 | 23.0 | 57.50 |

The procedure for preparing a batch of the above suspension takes place in two stages, i.e. the preparation of the gelatin base and the addition of the pharmaceutical agent.

The gelatin base is prepared by adding the gelatin to the deionized water at 30° C. and mixing until the gelatin is dissolved. The solution is then cooled to 25° C. and the mannitol, the sodium lauryl sulfate, the sweetener, and the flavors are separately added and dissolved.

The croscarmellose sodium in powder form (Ac-DiSol) and the taste-neutral spray dried acetaminophen powder are dry mixed and screened through a 20 mesh screen. The mixed powder is added to the gelatin solution and further admixed with a homomixer for thirty minutes to form a uniform dispersion.

The freeze drier employed in this example was a Virtis 25 SRC Model Freeze Drier. The fast dissolving dosage forms were prepared by dosing 500 milligrams of the suspension of acetaminophen into each well in a thermoformed blister tray containing 10 wells per tray. The filled trays were placed in a larger tray containing a dry ice-methanol mixture. When the suspension in the wells were frozen, the samples were placed on the freeze dryer trays at a shelf temperature of −45° C.

When the samples had reached a temperature of −45° C., as determined by a probe in a well, the condenser was turned on and the freezer turned off. The condenser temperature was brought to between −40° and 31 45° C. and the vacuum was turned on to between 50 and 60 millitorrs. The heater was then turned on and the shelf temperature was adjusted to 50°-55° C. The heat-dry cycle lasted for 4 hours. The vacuum, the condenser and the heater were turned off and the samples removed. The wafers from each batch were removed from the wells in the trays. They were white in color and each weighed about 165 milligrams of which about 80 milligrams was acetaminophen. The wafers from each batch when placed on the tongue exhibited a cherry/cream flavor with a very slight bitter aftertaste. When placed in water at 37° C. the wafers disintegrated in less than ten seconds.

EXAMPLE 5

This example describes the preparation of fast dissolving dosage forms using the spray dried taste neutral acetaminophen of Example 2 and other ingredients as follows:

| Ingredients | Weight % suspension | Grams in suspension |
| --- | --- | --- |
| Gelatin, BY 19/50 | 4.0 | 10.00 |
| Mannitol, granular | 3.0 | 7.50 |
| Deionized water | 67.10 | 167.75 |
| NUTRASWEET, NF | 1.20 | 3.00 |
| Cherry #271 | 0.40 | 1.00 |
| Cream Flavor #59.200/A | 0.20 | 0.50 |
| Sodium laurylsulfate | 0.10 | 0.25 |
| Croscarmellose sodium, Type A | 1.00 | 2.50 |
| Powder, Example 2 | 23.0 | 57.50 |

The procedure for preparing the suspension and the procedure for freeze drying the suspension were essentially the same as in Example 4. The wafers when placed on the tongue exhibited a cherry-cream flavor with a very slight bitter aftertaste. When placed in water at 37° C. the wafers disintegrated in less than ten seconds.

We claim:

1. A therapeutic taste neutral powder form of spray-dried acetaminophen which consists essentially of, based upon the weight of the powder, about 60% to 74% by weight acetaminophen and about 26% to 40% by weight of a copolymer, cationic in character, based on dimethylaminoethyl methacrylate and neutral methacrylic acid esters having a mean molecular weight of 150,000, the powder having been spray dried from a suspension of the acetaminophen in a solution of the copolymer in an organic solvent selective for the copolymer.

2. In a pharmaceutical dosage form for oral administration as a solid, which dosage form can be disintegrated by water within ten seconds, the improvement which comprises incorporating into such dosage form as the pharmaceutical substance a therapeutic taste-neutral powder form of spray-dried acetaminophen which consists essentially of, based upon the weight of the powder, about 60% to 74% by weight acetaminophen and about 26% to 40% by weight of a copolymer, cationic in character, based on dimethylaminoethyl methacrylate and neutral methacrylic acid esters having a mean molecular weight of 150,000, the powder having been spray dried from a suspension of the acetaminophen in a solution of the copolymer in an organic solvent selective for the copolymer.

3. In a pharmaceutical dosage form for oral administration as a solid chewable taste-neutral tablet containing acetaminophen, the improvement which comprises incorporating into such tablet as the pharmaceutical substance a therapeutic taste-neutral powder form of spray-dried acetaminophen which consists essentially of, based upon the weight of the powder, about 60% to 74% by weight acetaminophen and about 26% to 40% by weight of a copolymer, cationic in character, based on dimethylaminoethyl methacrylate and neutral methacrylic acid esters having a mean molecular weight of 150,000, the powder having been spray dried from a suspension of the acetaminophen in a solution of the copolymer in an organic solvent selective for the copolymer.

4. The spray-dried acetaminophen of claim 1 wherein the organic solvent is methylene chloride.

5. The pharmaceutical dosage form of claim 2 wherein the organic solvent is methylene chloride.

6. The pharmaceutical dosage form of claim 3 wherein the organic solvent is methylene chloride.

* * * * *